United States Patent [19]

Chen et al.

[11] Patent Number: 5,569,366
[45] Date of Patent: Oct. 29, 1996

[54] FLUORESCENT LABELLED CARBOHYDRATES AND THEIR ANALYSIS

[75] Inventors: Fu-Tai A. Chen; Ming-Sun Liu, both of Brea; Ramon A. Evangelista, Placentia, all of Calif.

[73] Assignee: Beckman Instruments, Inc., Fullerton, Calif.

[21] Appl. No.: 380,917

[22] Filed: Jan. 27, 1995

[51] Int. Cl.$^6$ .................................................. G01N 27/26
[52] U.S. Cl. .......................... 204/452; 204/451; 204/461; 204/603; 204/601; 204/612
[58] Field of Search .......................... 204/182.8, 180.1, 204/182.6, 451, 452, 601, 603

[56] References Cited

U.S. PATENT DOCUMENTS

| | | | |
|---|---|---|---|
| 4,844,841 | 7/1989 | Koller et al. | 562/55 |
| 4,852,137 | 7/1989 | Mackay | 378/62 |
| 4,874,492 | 10/1989 | Mackay | 204/182.8 |
| 5,205,917 | 4/1993 | Klock | 204/182.8 |
| 5,215,883 | 6/1993 | Chu | 435/6 |
| 5,284,558 | 2/1994 | Linhardt et al. | 204/182.8 |

OTHER PUBLICATIONS

Electrophoresis, Anthony Andrews, Clarendon Press, Oxford 1986, p. 20.
Intro. to Modern Biochemistry, Academic Press, 1970, 3rd ed., Peter Karlson, p. 7.
Survey of Organic Syntheses, John Wiley, Calvin Buehler, 1973, p. 427.

*Primary Examiner*—Kathryn Gorgos
*Assistant Examiner*—Alex Noguerda
*Attorney, Agent, or Firm*—William H. May; Arnold Grant; Janis C. Henry

[57] ABSTRACT

Processes for the electrophoretic analysis of monosaccharides and/or polysaccharides are disclosed. The processes generally first include providing a composition having derivatized mono and/or polysaccharide components which are monosaccharide and/or polysaccharide labelled with a fluorescing charged compound. Then introducing the composition into an electrophoretic medium and applying an electric field across the electrophoretic medium causes the derivatized monosaccharide and/or polysaccharide components to differentially migrate within the electrophoretic medium. Then detecting the derivatized monosaccharide and/or polysaccharide components is accomplished by laser exciting the derivatized monosaccharide and/or polysaccharide components and monitoring fluorescent emission of the derivatized monosaccharide and/or polysaccharide components. The processes provide extremely low detection limits of the labelled components.

8 Claims, 13 Drawing Sheets

FLUORESCENT LABELLED CARBOHYDRATES AND THEIR ANALYSIS

BACKGROUND OF THE INVENTION

1. Field of the Invention

The present invention is related to saccharides, including mono-, oligo-, and polysaccharides and methods for their analysis. More particularly, the present invention relates to fluorescent labelled mono- and polysaccharides and electrophoretic methods for their analysis. Advantageously, the present invention provides for the analysis and detection of picomole quantities of saccharides.

2. Description of Relevant Art

The analytical separation and detection of carbohydrates, simple sugars and oligo- and polysaccharides have been the subject of developmental efforts for decades. Traditional methods for separating and detecting these compounds have relied upon chromatographic methods, e.g. gas chromatography and high pressure liquid chromatography, wet chemical methods, and slab gel electrophoresis. Because carbohydrates lack outstanding structural features, the detection of carbohydrates at extremely low detection limits has been difficult. Carbohydrates absorb in the ultraviolet spectrum at 185 nm but their molar absorptivities are low. Amperometric detection is more sensitive than uv detection but suffers in that it is nonspecific and will detect a wide variety of compounds including amines and alcohols.

The more recent focus in biological research on the role of glycoproteins and carbohydrates in the structure and function of living cells has lead to an increase in the effort to detect carbohydrates, sugars, and oligosaccharides in trace quantities. Mono and polysaccharide analytical applications in which very low detection limits are desirable include carbohydrate and glycoprotein sequencing methods, the discovery and identification of new carbohydrates and drug development. Capillary electrophoresis in combination with amperometric detection has yielded detection of mono and oligosaccharides at concentration in the micromolar range. However, much lower detection limits are a goal of many analytical chemists and researchers.

More recently, electrophoresis has become an analytical tool of choice for smaller quantities of saccharides. The introduction of fluorescent detection in combination with slab gel and capillary electrophoresis has enhanced the detectability of carbohydrates and saccharides. For example, researchers have labelled mono- and oligosaccharides with fluorescent compounds and then electrophoretically separated and detected the labelled mono- and oligosaccharides. One of the earliest applications of fluorescent labelled sugars in slab gel electrophoresis was the reductive amination of sugars with 2-aminopyridine (AP). The AP reacts with the reducing end of mono- and polysaccharides. When the saccharide vicinal hydroxyls are complexed with borate at high pH (>10), or the amine functionalities are protonated at low pH <2.5), to form a charged compound, the labelled saccharide can be electrophoretically separated and detected with a fluorescent detector.

Another approach to the separation and detection of saccharides involves the reductive amination of monosaccharides and oligosaccharides with 8-aminonaphthalene-1,3,6-trisulfonic acid (ANTS) followed by their electrophoretic separation and detection utilizing a CCD fluorescence imaging device. ANTS labelled oligosaccharides have been separated and detected also using capillary electrophoresis techniques. Other reagents which fluoresce and react with the reducing ends of saccharides or aminated saccharides include 5-aminonaphthalene-2-sulfonate (ANA) 3-(4-carboxybenzoyl)- 2-quinolinecarboxaldehdye (CBQCA), 4-aminobenzonitrile (ABN).

The above described fluorescing reagents used in combination with common fluorescent detectors and capillary electrophoresis offer enhanced detectability of mono- and polysaccharides. Notwithstanding the improvement in saccharide detection made possible by these reagents and methods, there is a continuing need for analytical techniques which provide for even lower detection limits for carbohydrates, monosaccharides, oligosaccharides, and polysaccharides.

SUMMARY OF THE INVENTION

The present invention provides improved analytical processes for analyzing sugars and carbohydrates including mono-, oligo- and polysaccharides as well as sugar or carbohydrate containing compounds. As used herein the terms mono- and polysaccharides include sugars, carbohydrates and compounds containing sugar and/or carbohydrate functionalities. The processes of the present invention provide enhanced detectability of trace amounts of mono- and polysaccharides and require only microliter sample quantities.

More particularly, processes of the present invention provide for the electrophoretic separation and analysis of monosaccharides and/or polysaccharides and include first providing a composition having derivatized mono and/or polysaccharide components. The derivatized mono and/or polysaccharide components are the mono and/or polysaccharide components labelled with a fluorescing charged compound. Next introducing the composition into an electrophoretic medium and applying sufficient electric field across the medium causes the derivatized monosaccharide and/or polysaccharide components to migrate differentially with respect to each other within the electrophoretic medium. Detecting the derivatized monosaccharide and/or polysaccharide components is accomplished by laser induced fluorescence which involves using a laser to excite the derivatized monosaccharide and/or polysaccharide components and monitoring the fluorescent emission of the derivatized monosaccharide and/or polysaccharide components.

In preferred processes of the present invention, the electrophoretic medium is contained within a capillary column, the fluorescing charged compound is 9-aminopyrene- 1,4,6 trisulfonic acid and the excitation laser is an argon ion laser. Thus, the processes described herein are particularly adaptable to capillary electrophoresis systems which are equipped with argon ion laser induced fluorescence detectors.

The processes of the present invention feature the ability to utilize selected excitation wavelengths for which monosaccharide or polysaccharide derivatives have a high molar absorptivity a resulting high emission quantum efficiency. The processes of the present invention additionally feature the ability to electrophoretically separate and detect monosaccharide and/or polysaccharide coupled with a fluorescing compound in the presence of excess uncoupled fluorescing compound because when suitable laser induced fluorescence is utilized the excitation wavelengths are sufficiently different to allow their separate detection.

These and other advantages associated with the present invention will become apparent to those skilled in the art upon an understanding of the invention as described in the detailed description of the invention taken in combination with the following drawings.

DETAILED DESCRIPTION OF THE INVENTION

Figure 1:
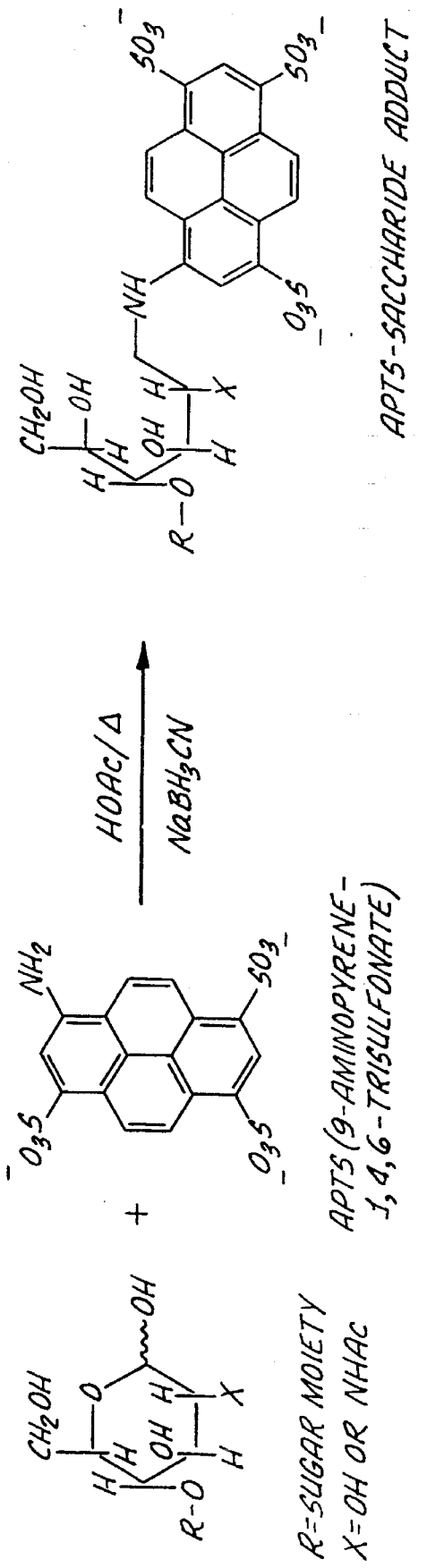
FIG. 1 illustrates an exemplary reductive amination reaction between 9-aminopyrene-1,4,6-trisulfonate (APTS) and a saccharide.

The present invention provides methods for the electrophoretic separation and detection of monosaccharides and/or polysaccharides including simple sugars, oligosaccharides, carbohydrates and glycoproteins. A wide range of analytical applications are benefitted by the present invention including carbohydrate and glycoprotein sequencing, industrial sugar and carbohydrate analytical procedures, drug analysis, and diagnostic procedures. Because the present invention provides for the detection of extremely small quantities of monosaccharides and polysaccharides those applications requiring very low detection limits are particularly benefitted by the present invention. In particular, those skilled in the art will appreciate that the ability to readily detect picomole quantities of monosaccharides and polysaccharides is very desirable in the analysis of carbohydrate and glycoprotein sequencing reaction products and the diagnostic analysis of biological samples.

The present invention provides processes which are particularly beneficial in connection with the use of capillary electrophoresis systems adaptable to a laser induced fluorescence detector. Such systems include the P/ACE series Capillary Electrophoresis Systems manufactured and sold by Beckman Instruments, Inc., Fullerton, Calif. However, the processes described herein have applicability on any electrophoresis system which is adaptable with a laser induced fluorescence detector.

Generally, the present invention provides processes for the electrophoretic analysis of monosaccharides and/or polysaccharides using laser induced fluorescent detection techniques. In contrast to prior art fluorescent detection methods laser induced fluorescence detection provides extremely low detection limits. More particularly the monosaccharide and/or polysaccharide processes of the present invention include first providing a composition having derivatized mono and/or polysaccharide components. The derivatized components are monosaccharide and/or polysaccharide labelled with a fluorescing charged compound. Then introducing the composition into an electrophoretic medium and applying sufficient electric field across the electrophoretic medium causes the derivatized monosaccharide and/or polysaccharide components to differentially migrate within the electrophoretic medium. Detecting the derivatized monosaccharide and/or polysaccharide components is accomplished by a laser induced excitation of the derivatized monosaccharide and/or polysaccharide components and monitoring fluorescent emission of the derivatized monosaccharide and/or polysaccharide components.

As already mentioned, monosaccharides and polysaccharides suitable for analyzing according to the present invention include sugars, carbohydrates, glycoproteins, and compounds containing such sugars, carbohydrates, and glycoproteins. Unlike prior art processes for analyzing derivatized sugars and surprisingly, the processes of the present invention are applicable to reducing sugars as well as ketoses or nonreducing sugars. The particular source of monosaccharides and polysaccharides is not critical and the source can be natural, including animal and plant sources, or synthetic. As will be explained below, the monosaccharide or polysaccharide need not be pure and the derivatization reaction and electrophoresis procedure can be carried out without purification steps. Suitable specific sources include glycoproteins isolated and studied by researchers in the area of glycobiology, the products of carbohydrate and glycoprotein sequencing reactions, and samples synthesized and screened for diagnostic and therapeutic applications.

In accordance with the present invention derivatized monosaccharide and polysaccharide compounds are monosaccharides and polysaccharides which have been labelled with a fluorescing compound. In order for analytes to migrate under electrophoretic conditions they must carry a charge and since many carbohydrates are not charged, the fluorescing compounds are preferably charged. As described in more detail below, fluorescing compounds such as 9-aminopyrene-1,4,6-trisulfonic acid (APTS) and 8-aminonaphthalene-1,3,6-trisulfonate (ANTS) are particularly suitable in the practice of the present invention. The structure of these compounds is as follows:

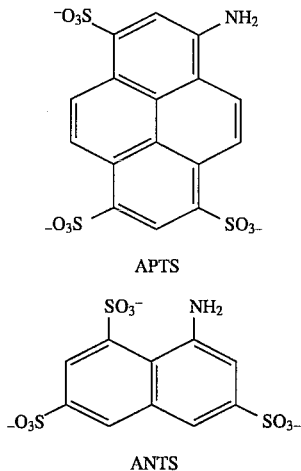

APTS

ANTS

APTS and ANTS feature amino functionalities which readily react with reducing sugars or saccharides and the reducing end of carbohydrates, including oligosaccharides and polysaccharides. As described below, and unlike prior art carbohydrate analysis techniques, APTS unexpectedly also reacts with ketoses and therefor provides a mechanism for the analysis of nonreducing sugars.

Reductive amination reactions are known in the art and those skilled in the art are credited with the ability to readily perform such reactions. Typically such reactions involve mixing the sugar or polysaccharide and fluorescing compound in the presence of a reducing agent at an elevated temperature. Once the reductive amination is complete the result is the formation of monosaccharides and polysaccharides which are labelled with a fluorescing compound. Although ANTS and particularly APTS are preferred fluorescing compounds those skilled in the art will recognize that other charged fluorescing compounds with functionalities which are capable of reacting or complexing with sugars or carbohydrates can be used. Such reactions or complexes can include complexes such as site specific interactions which do not involve the formation of covalent bonds between the sugar and fluorescing compound.

As a feature of the present invention, there is no requirement to purify the derivatized monosaccharide or polysaccharide and the reaction solution containing excess nonreacted fluorescing compound and derivatized monosaccharide and/or polysaccharide is ready for electrophoretic separations. As demonstrated below, this is possible because the fluorescing compound and the corresponding derivatized monosaccharide and/or derivatized polysaccharide have different excitation and emission spectra. Thus, when the excitation wavelength is judiciously selected, the relatively large amount of excess fluorescing compound does not interfere in the electropherogram.

While standard slab based electrophoresis techniques can be used in the practice of the present invention, the preferred electrophoresis technique is capillary electrophoresis. Because the present invention offers uniquely low detection limits, the use of capillary electrophoresis and its inherently small sample volumes offers the advantage of detecting tremendously small amounts of monosaccharide and/or polysaccharide fluorescent labelled derivatives. Capillary electrophoresis procedures have been in use for several years and those skilled in the art are credited with the ability to perform general electrophoretic analyses.

Capillaries having utility in the processes described herein can be fabricated from any substance having suitable physical strength and electric field stability, including organic polymeric material and inorganic materials. The preferred material is silica. Capillary sizes will vary according to the system used and the particular analysis. Typical diameters are less than 500 μm and usually less than 100 μm. Similarly, the length can be longer than 100 cm but usually is less than 100 cm. For purposes of the embodiments described herein, the diameters are about 20 μm to about 50 μm and the overall length about 27 cm. In most cases the capillary need only be adaptable to the electrophoresis system in use. One such electrophoresis system is the P/ACE series capillary electrophoresis instruments available from Beckman Instruments, Inc., Fullerton, Calif.

In accordance with the present invention, suitable electrophoretic mediums include aqueous inorganic or organic buffer solutions. Those skilled in the art recognize that universally the capillary electrophoretic analysis of sugars and carbohydrates typically involve the exclusive use of borate buffers. Surprisingly, it has been discovered that the present invention can be practiced using a variety of electrophoretic mediums including borate buffers, phosphate buffers, and organic salts such as morpholine based adducts. Buffer concentrations can vary depending upon the desired pH and the desired degree of electroosmotic flow. Typical electrophoretic medium concentrations are 50 mM to 250 mM of buffer compound.

The field strength or the applied electric field will vary with a number of factors. For example, the higher the electrophoretic medium buffer concentration, the higher the developed current and heat generation in the electrophoresis medium. Also, migration times will decrease with high voltage. Thus, when very short migration times are desired, the voltage is increased. It is not increased to the point where the temperature is detrimentally high. Nor is it increased so that no separation of the composition components occurs. Thus, the choice of applied voltage will vary with other analytical conditions. Those skilled in the art are credited with selecting such conditions.

In accordance with the present invention detecting the electrophoresis monosaccharide and/or polysaccharide derivatives involves the use of laser induced fluorescence detectors such as the detector system and detection processes described in U.S. Pat. No. 4,675,300. Such detectors can be adapted to commercially available electrophoresis instruments and generally involve the use of coherent energy from a laser to excite fluorescent or fluorescent labelled compounds. The emission radiation from the excited fluorescent compound is monitored by a photo sensitive device. A suitable laser induced fluorescence detector which is also adaptable to the P/ACE electrophoresis system is available from Omnichrome, Chino, Calif.

Preferably the laser is a He/Cd laser or an argon-ion laser. In preferred embodiments in which APTS is the fluorescent compound the most preferred laser is an argon-ion laser. As will become clear in the examples discussed below, when the 488 nm argon line is used to excite APTS and APTS derivatized monosaccharides and polysaccharides, the fluorescent emission of the APTS derivatized monosaccharides and polysaccharides is substantially higher in intensity than the APTS emission. The APTS derivatized monosaccharides and polysaccharides have an emission maximum at 512 nm while the APTS has an emission maximum at 501 nm. This difference in wavelength maximum is surprisingly advantageous because the excess derivatization reagent does not produce significant interference with signals from the derivatized compounds. Moreover, the 488 nm excitation is also less likely to produce interferences from endogenous fluorescent compounds in biological fluids which typically require lower wavelength excitation.

Unlike prior art detection systems the combination of laser induced fluorescence and capillary electrophoresis of the present invention provides the ability to detect picomole quantities of monosaccharides and polysaccharides. As will become clear in the discussion below, this ability is due to the strong excitation abilities of lasers and the particular absorption and emission spectra of fluorescent dyes.

The examples which follow are offered as descriptive of certain embodiments. As such they are exemplary only and are not limiting in their nature.

EXAMPLE 1

The following discussion relating to specific reactions conditions describe methods for preparing derivatized monosaccharides and/or polysaccharides for use in the processes of the present invention. In this example, and those that follow the polysaccharides which are derivatized and analyzed have the general polysaccharide structure shown in the reductive amination reaction scheme of FIG. 1. Monosaccharides contain only one sugar unit. As illustrated in FIG. 1 the exemplary reductive amination process involves reacting a saccharide with cyanoborohydride.

One derivatization reaction involved first mixing 10 µL of a 0.1 M saccharide solution (1 µm) with of 0.1 M APTS in 25% acetic acid and 10 µL of a 1 M sodium cyanoborohydride in tetrahydrofuran (THF) in a 500 µL Eppendorf SafeLock conical microcentrifuge tube. After centrifuging the tube, the reaction mixture was heated in a water bath at 75° C. for 1 hour.

Another derivatization reaction involved adding 2 pmole of maltoheptaose ($G_7$) in 10 µL water and following the same reaction conditions as described above. In a similar reaction, 200 nmoles of maltoheptaose ($G_7$) in 10 µL water was reductively aminated using the same reaction conditions and reactant volumes.

Another set of derivatization reactions involved reacting, in one reaction, 3 pmole and, in another reaction, 30 nmole of the oligosaccharide α-Glc-(1→6)-α-Glc-α-Glc-(1→4)-α-Glc-(1→4)-α-Glc ($G_4'$) using conditions and reactant volumes and amount as stated above.

The resulting mixtures of unreacted APTS and derivatized saccharides can be diluted with water and directly electrophoresed, directly electrophoresed undiluted, or purified and electrophoresed.

EXAMPLE 2

Figure 2:
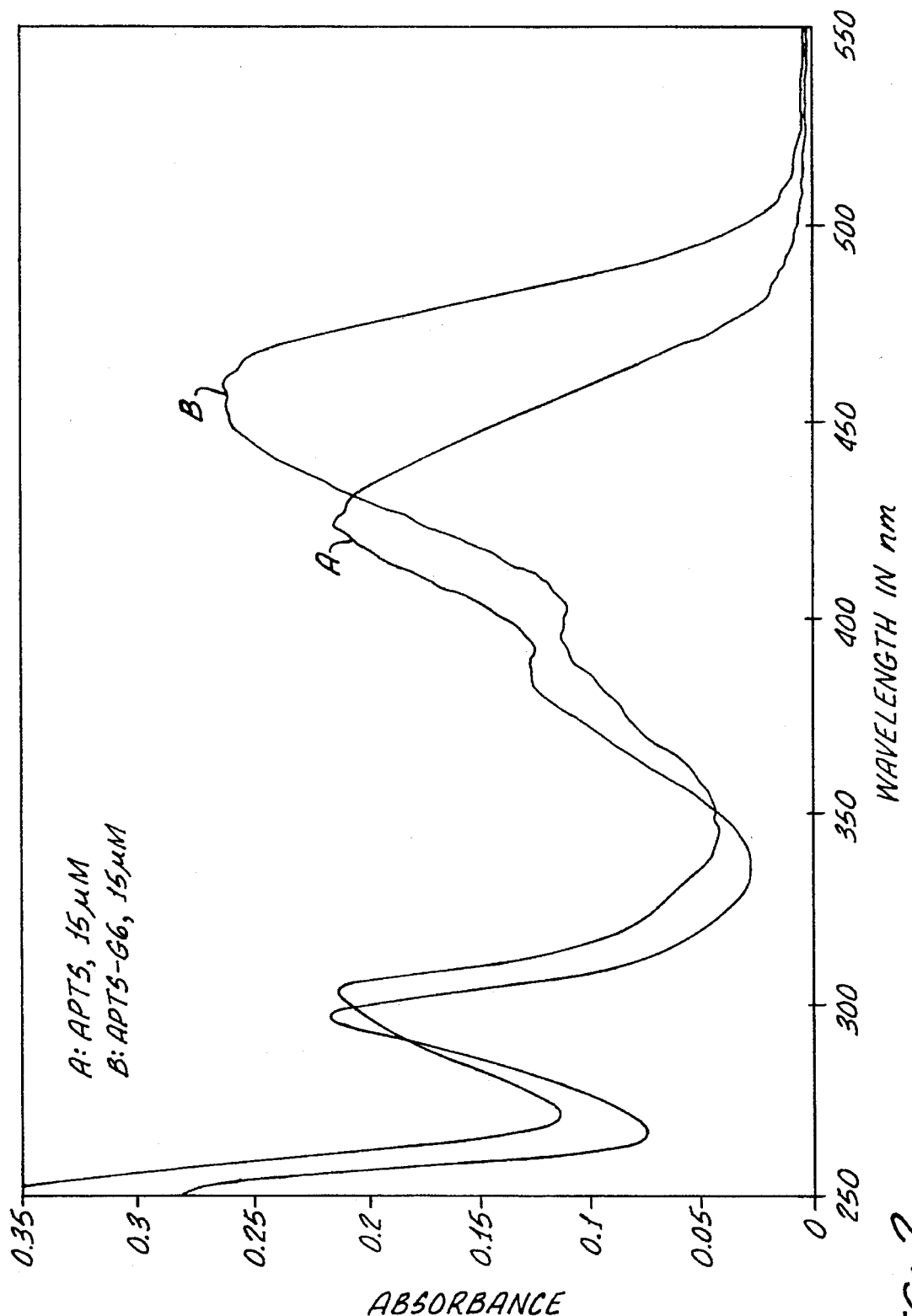
FIG. 2 shows UV/visible spectra of APTS (spectrum A) and APTS derivatized maltohexaose (spectrum B). The spectra were obtain with 15 μM concentration of each in 50 mM phosphate, pH 7.0.

In order to determine the UV/visible and fluorescence characteristics of APTS, ANTS, APTS derivatized saccharides, and ANTS derivatized saccharides, their individual UV/visible and fluorescence spectra were obtained. The UV/visible spectra were obtained on a Beckman 7500 diode-array spectrophotometer and the fluorescence spectra were obtained on a Perkin-Elmer LS50 Luminescence Spectrometer (Beaconsfield, Buckinghamshire, U.K.). The APTS and ANTS samples were prepared by dissolving them in 50 mM phosphate buffer, at pH 7.0. The ANTS and APTS ]derivatized saccharides were prepared as described above and then purified through a Sephadex G-10 column (5mm× 100 mm, using 50 mM bicarbonate buffer, at pH 8.5). FIG. 2 shows an exemplary UV/visible spectra of a 15 µM solution of APTS and a 15 µM solution of hexamaltose (($G_6$)). It clearly demonstrates the marked difference in the absorption spectra and indicates that the APTS derivatized saccharides absorb strongly at higher wavelengths than APTS.

Table 1 demonstrates the difference in emission wavelength maximum of APTS, APTS derived saccharides, ANTS and ANTS derived saccharides. The comparative fluorescent data is given for three different excitation wavelengths.

TABLE 1

Comparative fluorescence intensities of APTS, APTS-Rhamnose (APTS-Rham), APTS-$G_7$, ANTS, and ANTS-G7 at 1.0 µM each (RFU: relative fluorescence unit).

|  | Excitation:325 nm Emission $\lambda_{max}$:RFU | Excitation:442 nm Emission $\lambda_{max}$:RFU | Excitation:488 nm Emission $\lambda_{max}$:RFU |
| --- | --- | --- | --- |
| APTS | 502 nm:53.5 | 500 nm:186.8 | 501 nm:11.1 |
| APTS-G6 | 511 nm:95.9 | 511 nm:486.1 | 511 nm:155.4 |
| APTS-Rham | 514 nm:85.4 | 513 nm:403.9 | 513 nm:160.1 |
| ANTS | 507 nm:2.89 | 509 nm:0.254 | 505 nm:0.098 |
| ANTS-G6 | 506 nm:3.14 | 520 nm:0.318 | 506 nm:0.096 |
| ANTS-Rham | 512 nm:2.67 | 520 nm:0.307 | 517 nm:0.085 |

The data in Table 1 dramatically demonstrate the advantages associated with adopting a preferred embodiment of the present invention and using higher excitation wavelengths when. That is, by exciting compositions containing APTS and derivatized APTS with laser radiation having a wavelength of 488 nm and monitoring excitation at above 510 nm the detectability of APTS derivatized saccharides is extremely high. Advantageously, using the same excitation and emission conditions (488 nm excitation and over 510 nm emission), the detectability of underivatized APTS is very low and does not interfere with the detection of derivatized compounds. This is because when excited at 488 nm APTS absorbs only 4% of its absorption maximum (at 424 nm) while the APTS-derivatized sugars absorb about 35%.

As will be demonstrated below excitation at 488 nm is attained using a argon-ion laser line while excitation at 325 nm and 442 nm are attained using lines of a He/Cd laser. Thus, exciting with an argon-ion laser at 488 nm, coupled with detecting emission using a 520 nm narrow band filter, the fluorescence detection of APTS derivatized saccharides may be dramatically improved. In fact, when used in combination with argon-ion laser induced fluorescence, capillary electrophoresis techniques of the present invention provide exceedingly low detection limits.

EXAMPLE 3

The following example illustrates one embodiment of the present invention wherein APTS and APTS derivatized maltoheptaose ($G_7$) were electrophoretically separated. The maltoheptaose was derivatized according to the procedure generally described in Example 1. The reaction mixture was used directly and analyzed by capillary electrophoresis.

The analysis was performed on a P/ACE Series capillary electrophoresis system fitted with a laser induced fluorescence detector from Omnichrome, Chino, Calif. The detector consisted of a 5 milliwatt He/CD laser at 325 nm emission or an argon-ion laser at 488 nm emission and a laser headcoupler to a standard SMA-906 fiber connector to the P/ACE system. The emission filter was a 520 nm ±20 nm. The capillary column was an untreated silica having a total length of 27 cm (20 cm to detector window) and a diameter of 50 µm. The running buffer was 50 mM phosphate, at pH 2.2 and the sample injection involved a 20 second 0.5 psi pressure injection. The electrophoresis was performed using a voltage of 12 kV or 46 µA and between injections the capillary was sequentially washed with 1.0N NaOH and water with 12 seconds of 15 psi rinsing.

Figure 3:
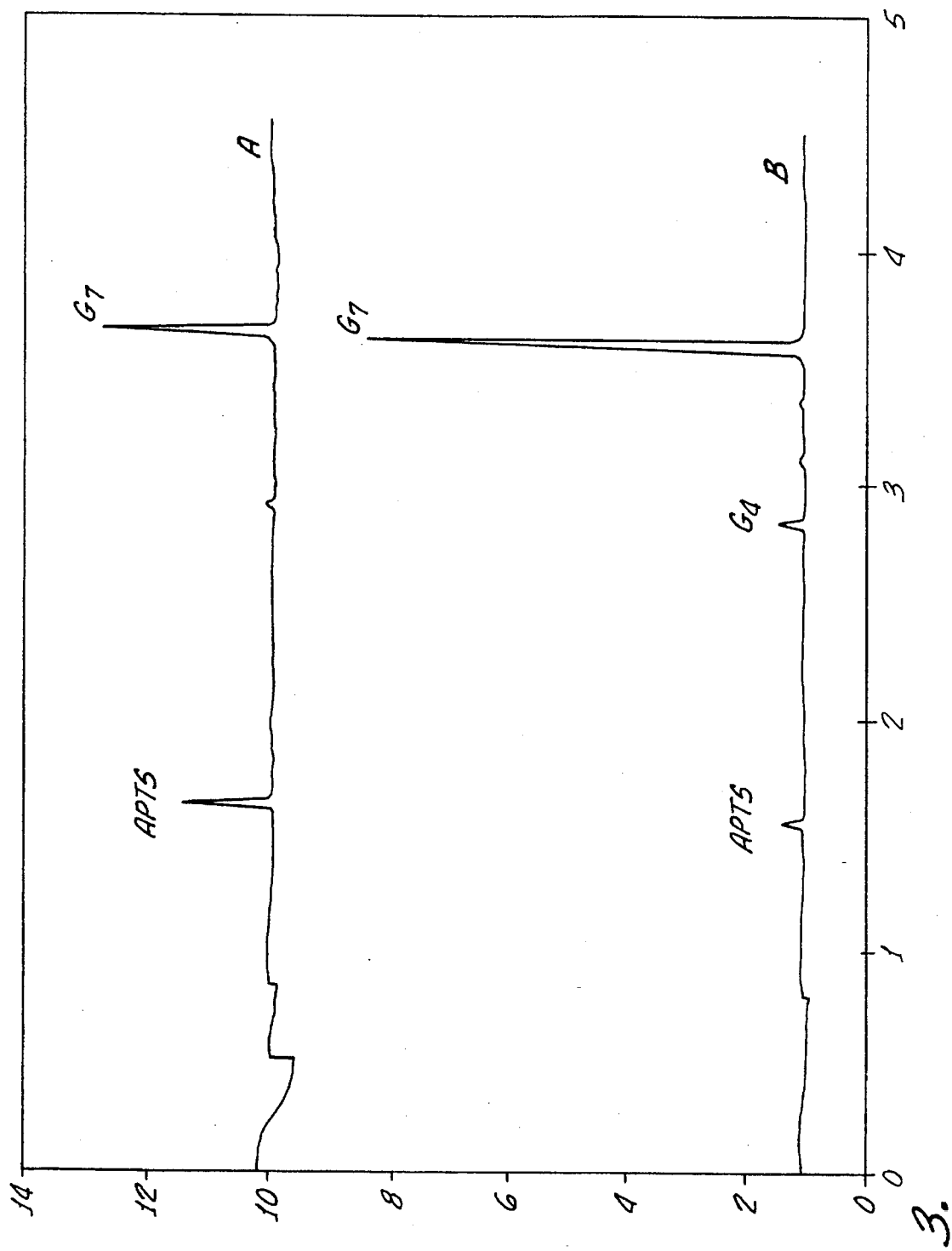
FIG. 3. shows two electropherograms of APTS and APTS-derivatized maltoheptaose using laser induced fluorescence techniques. Electropherogram A was obtained using an excitation wavelength of 325 nm (He/Cd laser) and electropherogram B was obtained using an excitation wavelength of 488 nm (argon-ion laser).

FIG. 3 shows the electropherograms resulting from the capillary electrophoresis separation. Electropherogram A was obtain with He/Cd laser induced detection (325 nm line) of a mixture of APTS and APTS-$G_7$ at 1.0 µm and 0.83 µm, respectively. Electropherogram B was obtained using the same conditions except excitation was with an argon-ion laser at 488 nm. This shows that the signal of APTS is about half of the APTS-$G_7$ signal with 325 nm excitation on an equal molar basis.

EXAMPLE 4

Figure 4:
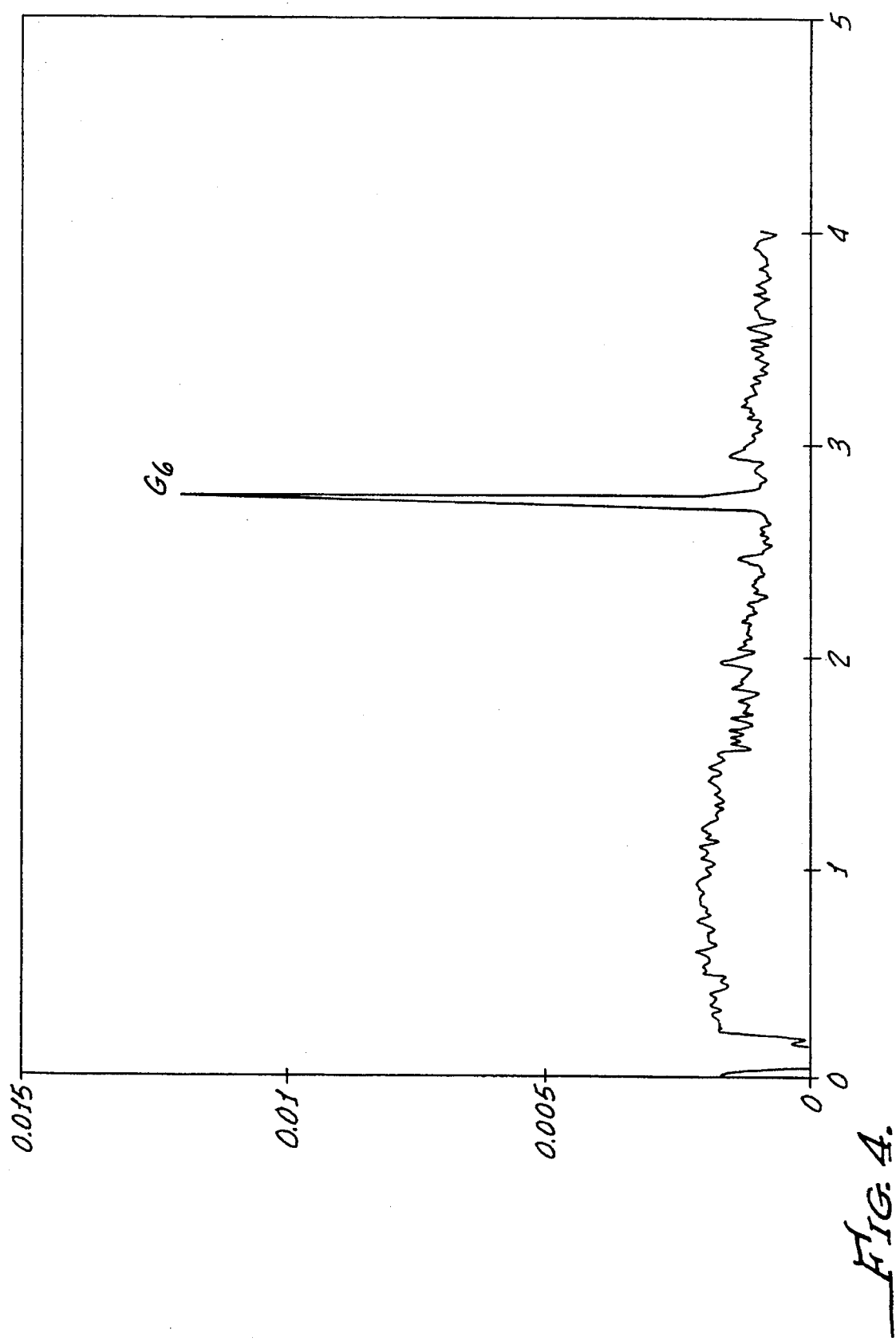
FIG. 4 is an electropherogram of APTS-derivatized maltohexaose.

In order to illustrate the low detectability of a oligosaccharide labelled with APTS the follow experiment was performed. Maltohexaose ($G_6$) was reductively aminated with APTS according to the general procedure outlined in Example 1. The resulting APTS-$G_6$ was purified using Sephadex G-10 column filtration and standard purification procedures. The purified APTS-$G_6$ solution was diluted to a concentration of 0.83 nMAPTS-$G_7$. An electropherogram was then obtained on a P/ACE instrument fitted with an laser induced fluorescence detector. An untreated fused-silica capillary having an internal diameter of 22 µm and an overall length of 27 cm. The excitation light source was a 488 nm argon-ion laser and the emission filter was 520 nm± 20nm (Oriel, Stratford, Conn.). A notch filter at 488 nm (Barr and Associates) was utilized and the applied potential was 20 kV/20 µA. Buffer conditions were 50 mM phosphate at pH 2.2 and the sample injection was a 30 second pressure injection. The capillary outlet was at the anode. FIG. 4 is the electropherogram obtained from the purified sample.

From this electropherogram, the limit of detection for APTS-derivatized sugars with 488 nm argon-ion excitation is estimated to be 0.4 nM (based on a signal/noise ratio of 10). With a sample injection of about 3 nanoliters, this amount of sugar detected is equal to 1.2 attomoles. This is significantly lower that the detection limit reported from other monosaccharide and polysaccharide analysis procedures.

EXAMPLE 5

In the area of glycobiology research, the ability to derivatize a saccharide or polysaccharide sample and then directly analyze the sample is very important. In order to illustrate the performance of the present invention in applications in which saccharides are derivatized and then directly analyzed by laser induced capillary electrophoresis the following experiments were performed.

In general the experiments involved preparing derivatized polysaccharides by reacting ten-fold decreasing amounts of saccharides with a constant excess amount of APTS and sodium cyanoborohydride in the manner described in Example 1. More particularly maltoheptaose ($G_7$) and α-Glc-(1→6)-α-Glc-(1→4)-α-Glc-(1→4)-α-Glc ($G_4'$) were reductively aminated with APTS. Then the prepared solutions were analyzed by capillary electrophoresis using a laser induced fluorescence detector system. The analytical conditions included using an untreated fused-silica capillary having an internal diameter of 20 µm and an overall length of 27 cm. The electrophoretic medium separation buffer was 200 mM borate at pH 10.2 and the applied potential was 20 kV/27 pA. The sample injection was a 30 second 0.5 psi pressure injection.

Figure 5:
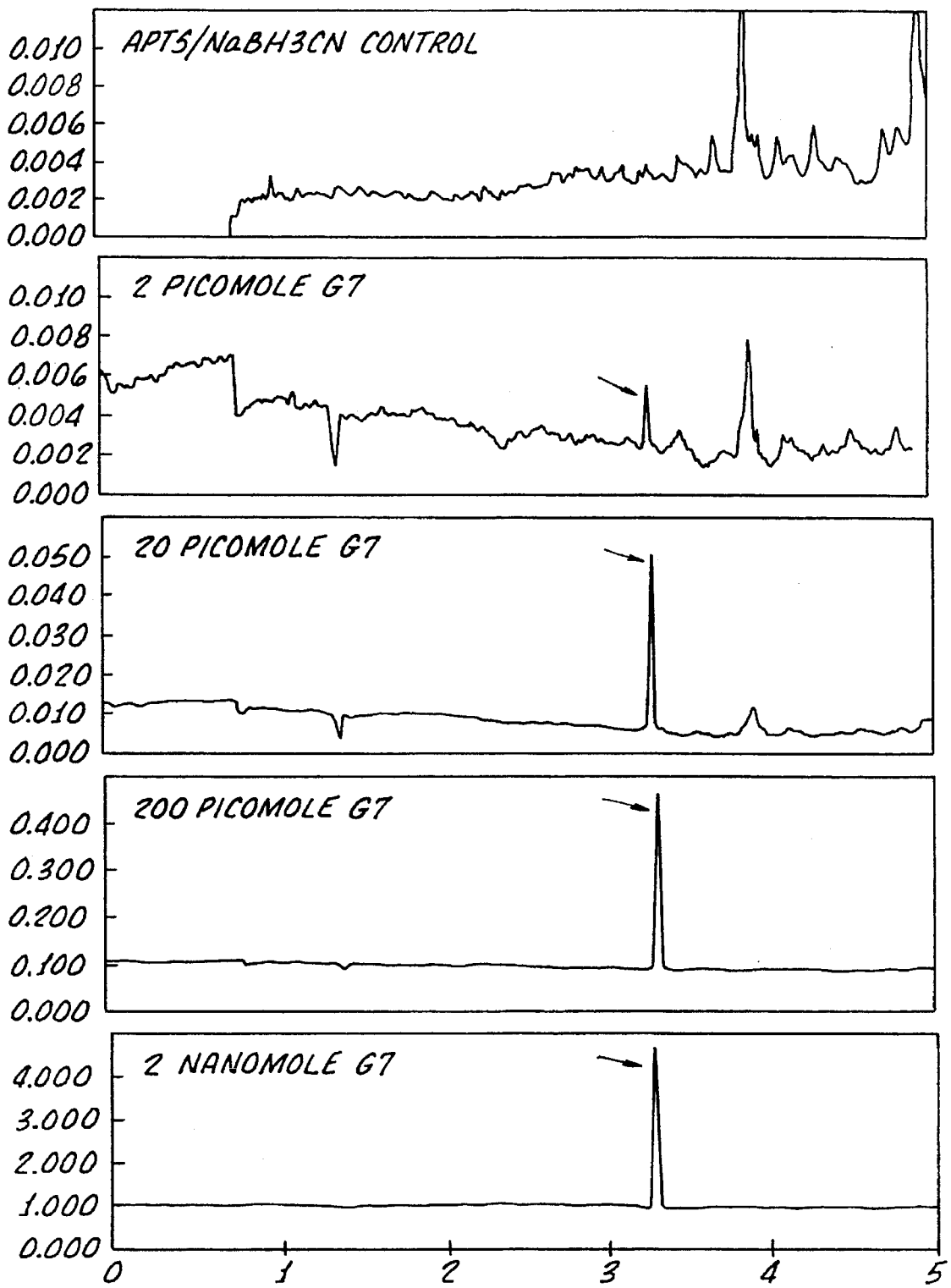
FIG. 5 is several electropherograms obtained using laser induced fluorescence detectors and samples consisting of a control and increasingly larger amounts of APTS $G_7$.

FIG. 5 shows electropherograms and laser induced fluorescence detector response for a control electropherogram and increasingly larger amounts of APTS $G_7$, beginning with 2 picomole APTS $G_7$ and up to 2 nanomoles of APTS $G_7$. These electropherogram show that in the analysis of derivatized polysaccharide analytes at amounts close to the detection limits, the fluorescent impurities present in the large excess of APTS appear in the electropherograms but the impurity peaks have longer migration times than the oligosaccharide-APTS peak. Furthermore, the excess APTS does not give a strong signal so it does not overpower the analyte signal.

Figure 6:
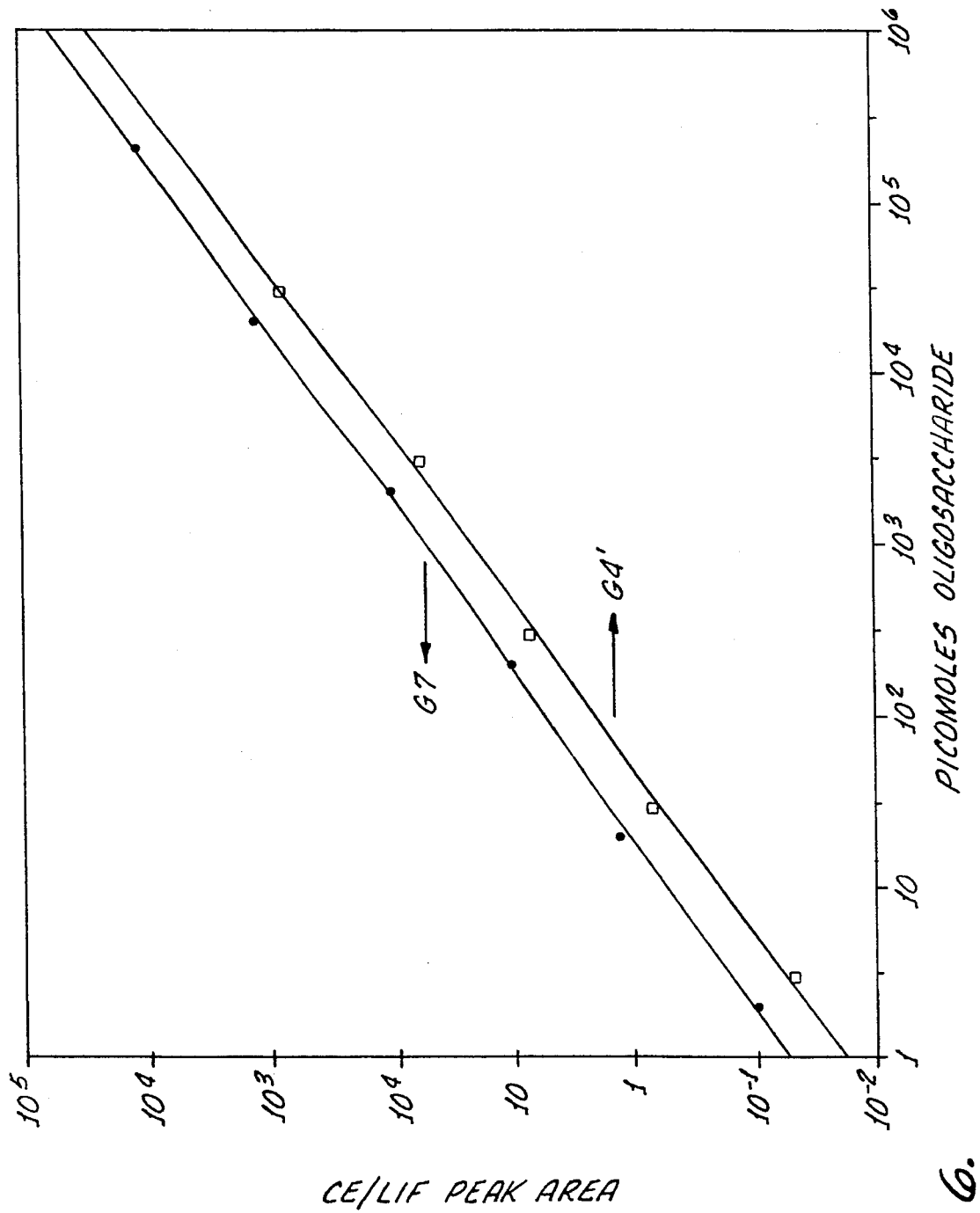
FIG. 6 is a plot which illustrates the linearity of APTS derivatized saccharides using laser induced detection. The plot gives signal as a function of amount of sugar in a derivatization mixture containing constant amount of APTS and $NaBH_3CN$.

FIG. 6 demonstrates the linear relationship between the amount of polysaccharide in the derivatization mixture over five orders of magnitude. The linear correlation between peak area and molar amount of sugar for both APTS $G_7$ (r = 0.99953) and APTS $G_4'$ (r = 0.99956) indicates that the efficiency of the reductive amination reaction is close to 100% In contrast to some processes which provide optimum fluorescence at a certain reagent/saccharide ratio, the present method produces a signal which is linearly proportional to the amount of saccharide regardless of the amount of excess reagent.

The results of these experiments further demonstrate that when analyzing diluted and unpurified reaction mixtures as little as 2 to 3 pmole of a saccharide can be derivatized and detected by the present capillary electrophoresis and laser induced fluorescence detection.

EXAMPLE 6

In the following example, the ability of the present invention to provide excellent analytical results for a series of monosaccharides are illustrated. A series of 9 monosaccharides were derivatized with APTS using the derivatization procedures described in Example 1. These 9 monosaccharides included fructose, a ketohexose and a nonreducing sugar. (The derivatization times for fructose were longer and included a reaction time of 2.5 hr at 75° C.) The 9 derivatized monosaccharides were analyzed using a fused-silica capillary having an internal diameter of 20 µm and an overall length of 27 cm. The emission light source was a 488 nm argon-ion laser and the emission filter was a 520±20 nm filter from Oriel, Stratford, Conn. The notch filter was at 488 nm. The applied potential was 20 kV/19 µA and the buffer was 100 mM borate at pH 10.2. The outlet was at the cathode.

Figure 7:
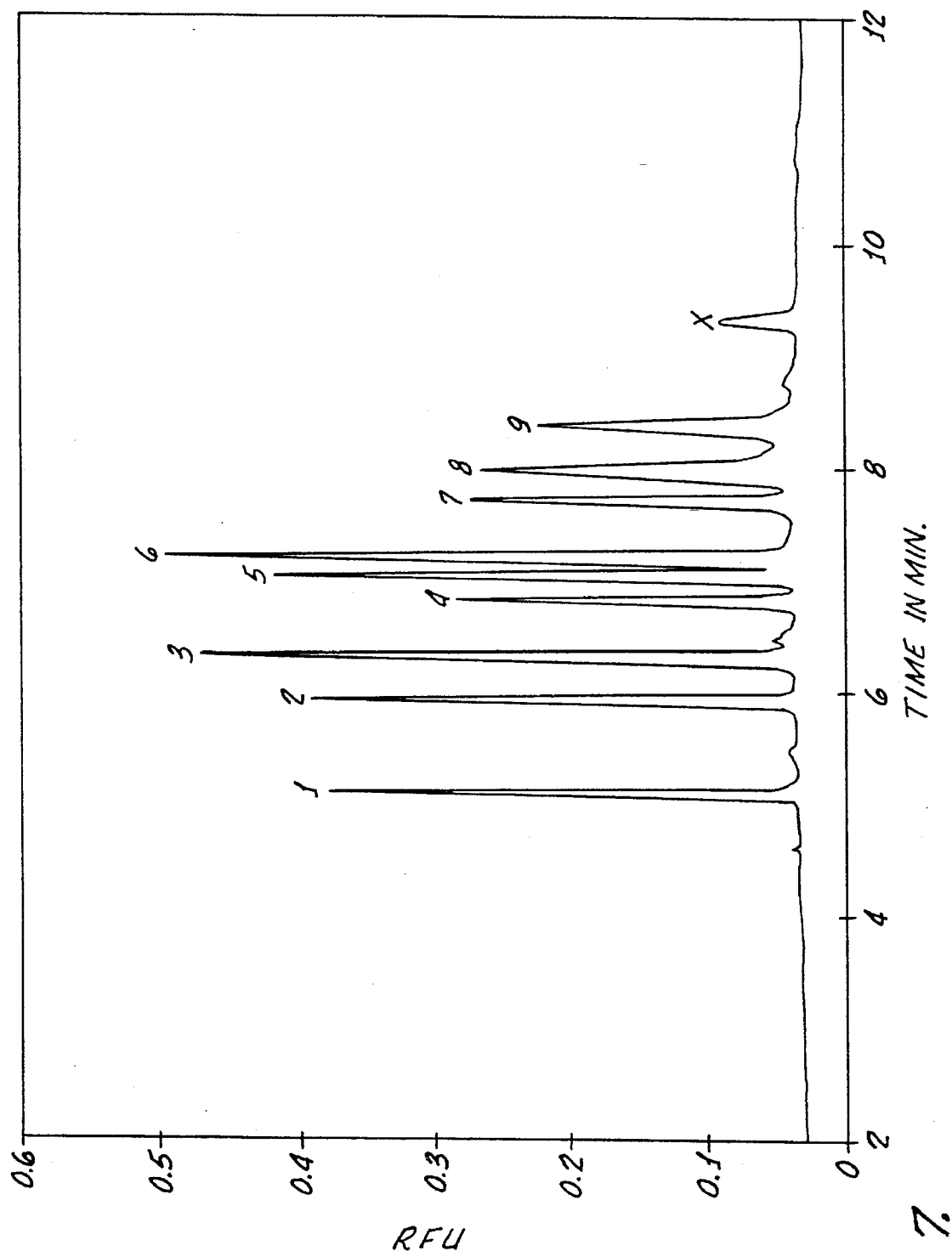
FIG. 7 Electropherogram of nine APTS-derivatized monosaccharides at 1.0 μM each.

FIG. 7 is an electropherogram obtained from the analysis of the 9 APTS derivatized monosaccharides. The peak identification is as follows: 1) N-acetylgalactosamine, 2) N-acetylglucosamine, 3) rhamnose, 4) mannose, 5) glucose, 6) fructose, 7) xylose, 8) fucose, 9) galactose. X) impurity peak derived from APTS. Differential complexation of borate from the buffer with polyhydroxyl moieties of the monosaccharide derivatives appeared to be primary mechanism of the capillary electrophoresis separation. Surprisingly, fructose, which in the past was not expected to derivatize under reductive amination conditions, was converted to the APTS derivative and effectively analyzed. Peak 6 in the FIG. 7 electropherogram is APTS fructose.

EXAMPLE 7

In order to compare gel electrophoresis with capillary electrophoresis, the analysis of a mixture of maltooligosaccharides was undertaken. Dextrin 15 from Fluka, Flushing, N.Y. was derivatized with APTS as described in Example 1. The capillary electrophoresis conditions included a running buffer of 50 mM phosphate at pH 2.2 and an applied potential of 25 kV/19 µA. The injection was a 20 second 0.5 psi pressure injection and the outlet was at the anode.

Figure 8:
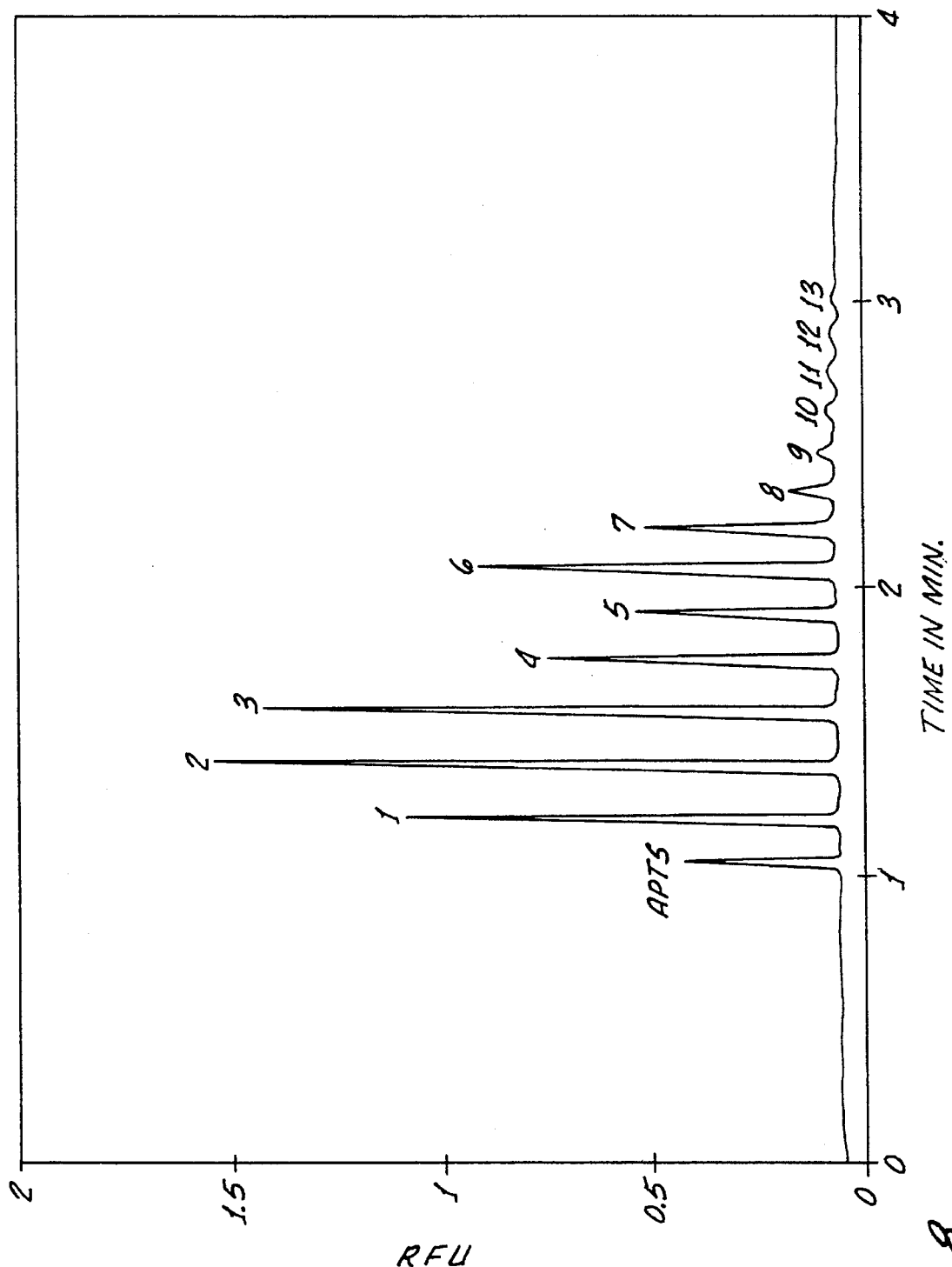
FIG. 8 is an electropherogram of a 1000-fold diluted APTS-dextrin 15 derivatization reaction mixture after 30 min reaction at 75° C.

FIG. 8 is an electropherogram obtained from separating the diluted and unpurified reductive amination reaction mixture of maltooligosaccharides. The electropherogram shows that excess APTS migrates at 1.05 min followed by the APTS-derivatized glucose ($G_1$), maltose ($G_2$), maltotriose ($G_3$) and etc, which are well-resolved and visible up to APTS-$G_{12}$. The electropherogram peak identification is as follows: 1) APTS-$G_1$, 2) APTS-$G_2$, 3) APTS-$G_3$, 4) APTS-$G_4$, 5) APTS-$G_5$, 6) APTS-$G_6$, 7) APTS-$G_7$, 8) APTS-$G_8$, 9) APTS-$G_9$, 10)APTS-$G_{10}$, 11) APTS-$G_{11}$, 12) APTS-$G_2$, 13) APTS-$G_{13}$ and etc.

Figure 9:
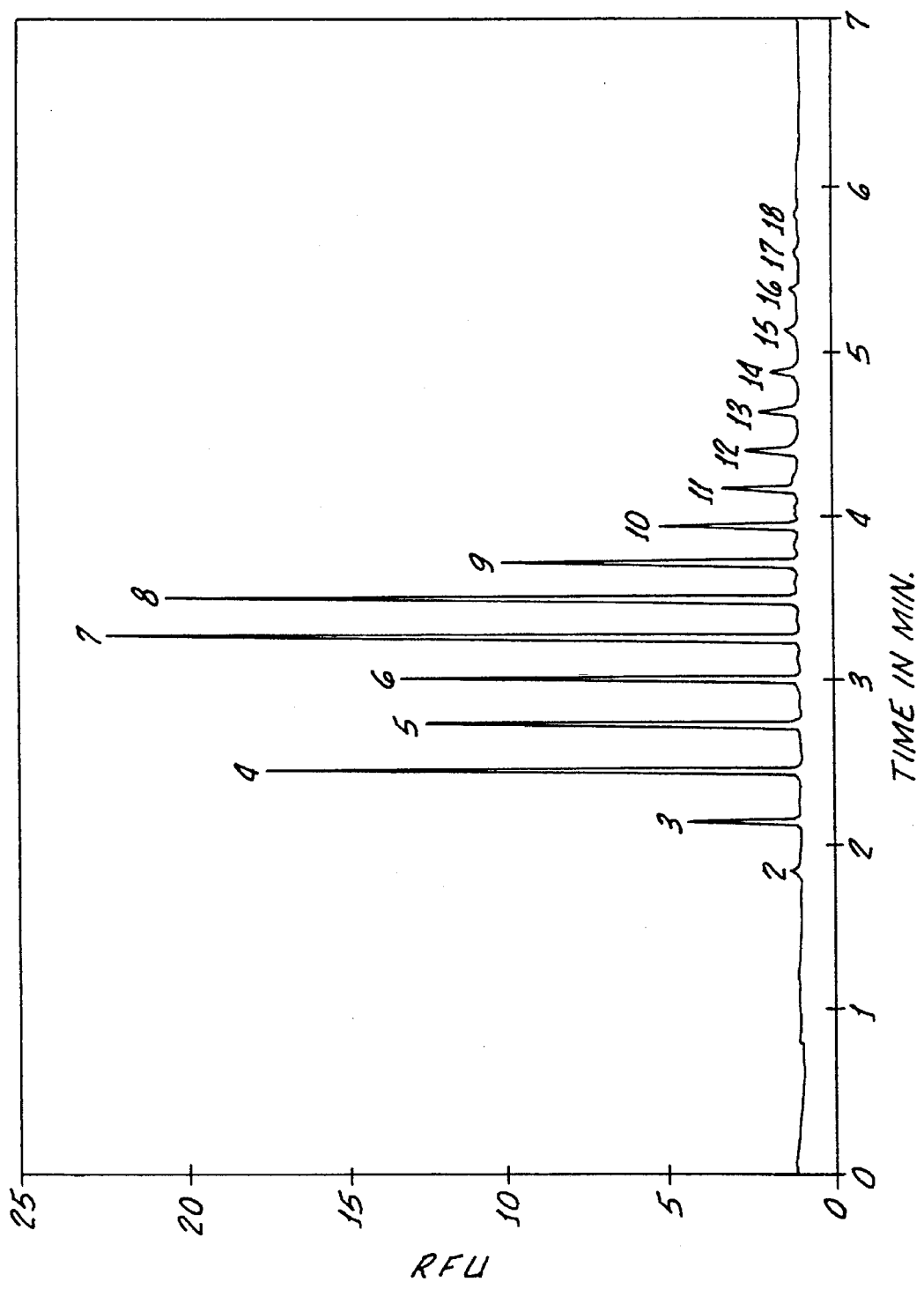
FIG. 9 is an electropherogram of a 1000 fold-diluted APTS derivatized dextrin 15 of FIG. 8 using a 22 μm capillary with a 20 kV applied potential.

The reductive amination reaction mixture was then purified by gel filtration through a Sephadex G-10 column. The purified mixture was analyzed by polyacrylamide gel electrophoresis (PAGE) using standard slab electrophoresis procedures and conditions which included a 30% polyacrylamide gel electrophoresis system with fluorescent excitation by 366 nm UV lamp. Capillary electrophoresis was also performed using argonion laser induced fluorescence (488 nm line) detection as described in the preceding paragraph. The capillary electrophoresis analysis was performed after a 1000-fold dilution of the mixture. FIG. 9 illustrates the electropherogram obtained from the capillary electrophoresis analysis. The PAGE analytical systems resolved the oligosaccharides. The capillary electrophoresis system in combination with the laser induced fluorescence, provided baseline resolution even with a 1000-fold diluted sample.

EXAMPLE 8

In order to study the effects of a change in electrophoretic medium on the analytical results the following experiment was performed. The Sephadex gel-filtration purified APTS-dextrin 15 was subjected to capillary electrophoresis using a 200 mM borate buffer electrophoresis medium at pH 10.2 rather than the phosphate buffer used in Example 7. The applied potential was 17 kV/36 µA. In this case the outlet is the cathode.

Figure 10:
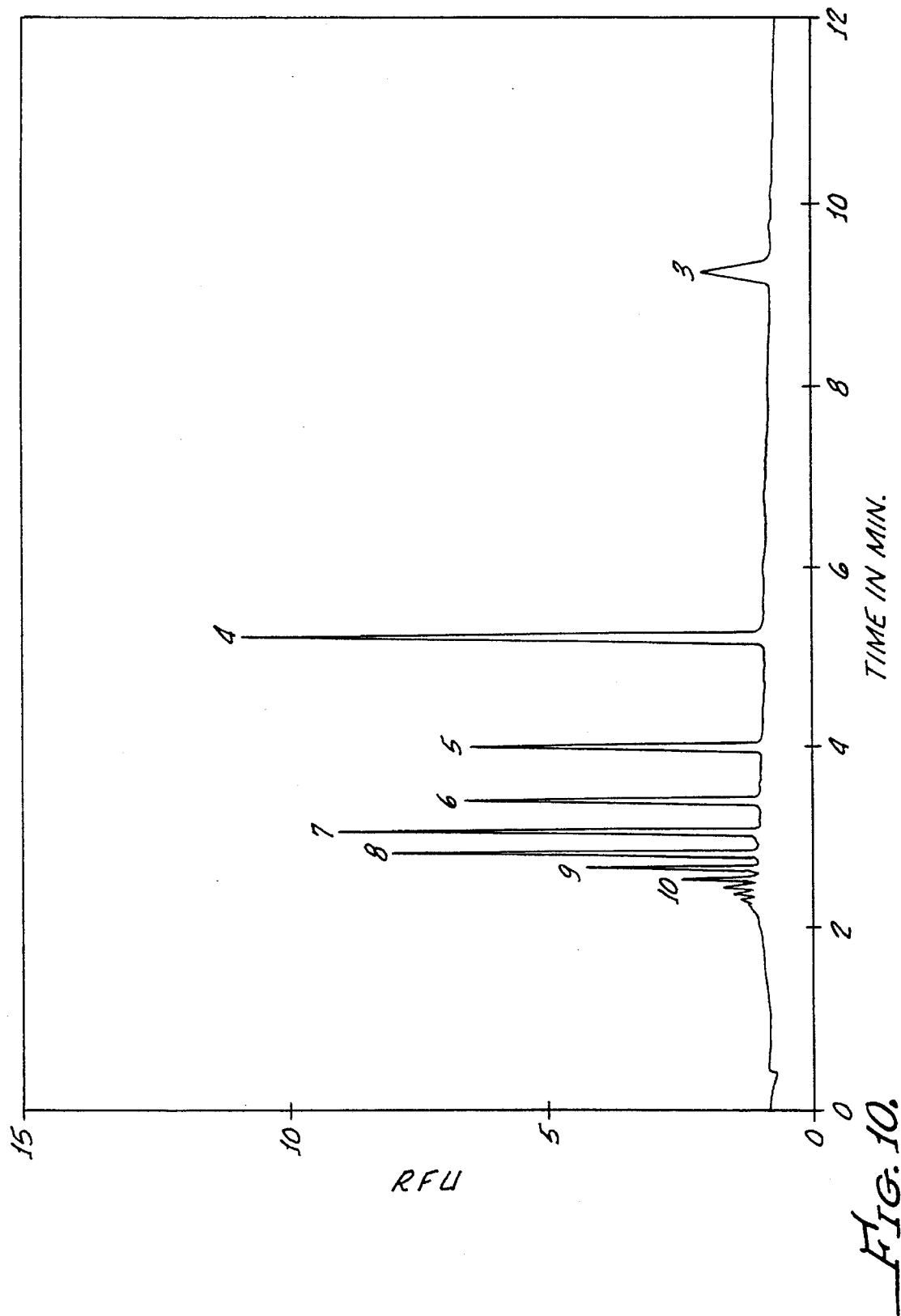
FIG. 10 is an electropherogram of the APTS-derivatized dextrin 15 of FIG. 8 using the same conditions except that the buffer was 200 mM borate pH 10.2 and the applied potential was 17 kV/36 μA.

FIG. 10 is the electropherogram obtained from electrophoretically separating the gel-filtration purified APTS-dextrin 15 using the detection system described in Example. The electropherogram shows that larger oligosaccharide derivatives of APTS migrate faster than the smaller oligosaccharide species. The electroendoosmotic flow marker occurs at 1.1 min. This electrooendosmotic flow provides a fixed velocity component that sweeps both neutral and ionic species, regardless of charge, toward the cathode. All APTS-derivatized components of the APTS dextrin are also attracted towards the anode due to their negative charges, against the electroendoosmotic flow, at their own velocity according to their intrinsic electrophoretic mobilities. Thus, each APTS-saccharide has its own net migration velocity. Since the electroendoosmotic velocity is greater than the intrinsic electrophoretic mobility of each APTS-saccharide, all species migrate towards the cathode. The APTS and the derivatized glucose ($G_1$), maltose ($G_2$) are absent from the electropherogram of Fig due to their high electrophoretic mobility toward the anode which is against the velocity of the electroendoosmotic flow. Within the analytical timeframe of 10 minutes they do not reach the detector.

EXAMPLE 9

The following example illustrates the utility of the present invention in the study of a glycosidase-catalyzed reaction.

Figure 11:
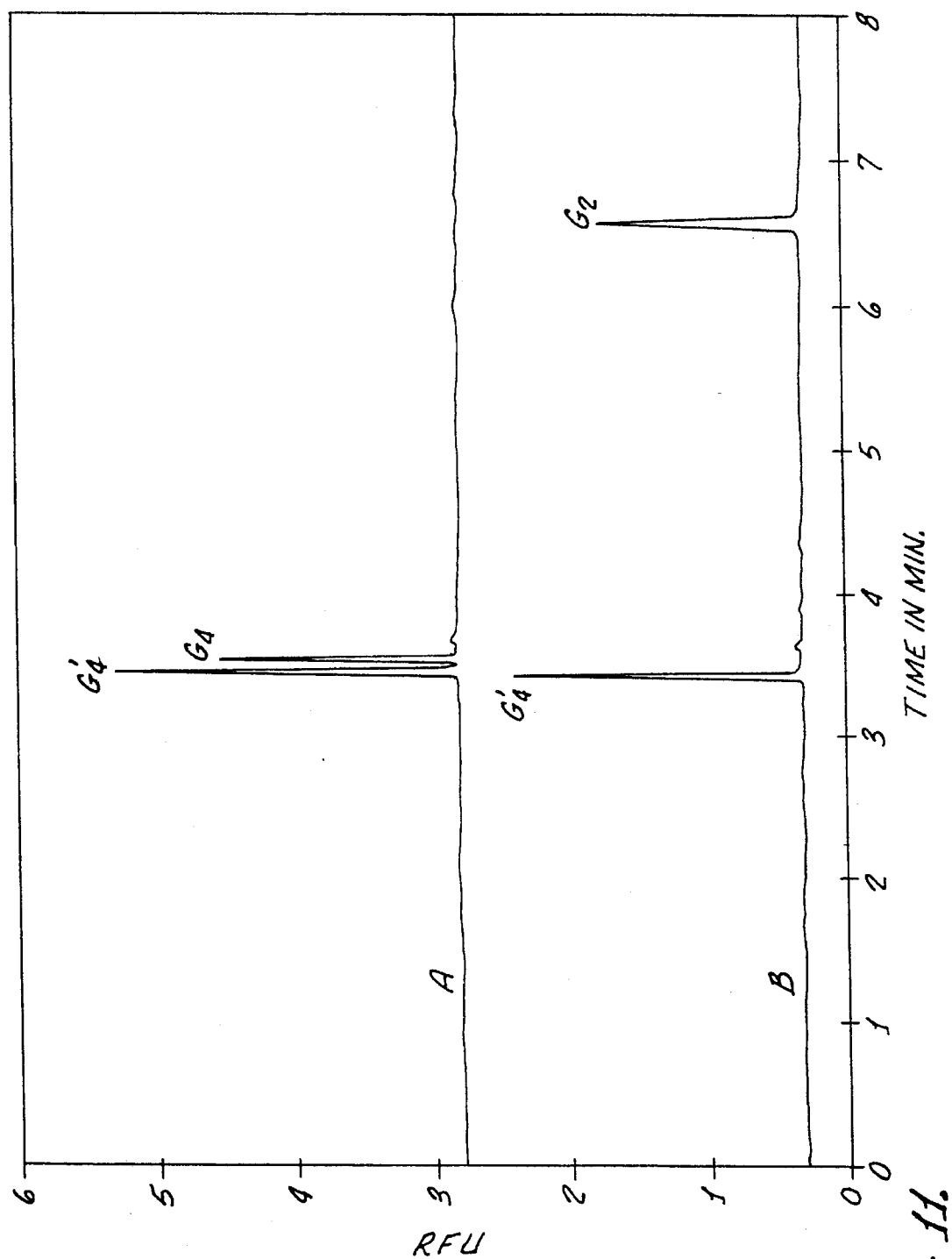
FIG. 11 shows two electropherograms of a mixture of APTS-$G_4$' and APTS-$G_4$' in borate buffer. Electropherogram B was obtained after an amylase catalyzed hydrolysis of the mixture used to obtain electropherogram A.

APTS derivatized maltotetraose, α-Glc-(1→4)-α-Glc-(1→4)-α-Glc-(1→4)-α-Glc ($G_4$) and its structural isomer, α-Glc-(1→6)-α-Glc-(1→4)-α-Glc-(1→4)-α-Glc ($G_4'$) were prepared as generally described in Example 1. The electrophoretic separation of these structural isomers was achieved in 150 mM borate buffer with baseline resolution using the capillary electrophoresis system described in Example. Electropherogram A in FIG. 11 illustrates the results of this separation. The analysis conditions were the same as those used to obtained the electropherogram of FIG. 5 except the running buffer was 150 mM borate pH 10.2 and the applied potential was 20 kV/21 µA. The outlet end was the cathode. Electropherogram B is that of α-amylase-catalyzed hydrolysis product of APTS-$G_4$ and APTS-$G_4'$ mixture 60 min after the addition of 5 µL of α-amylase (100 µg/mL) to the 100 µL sample used to obtain electropherogram A.

The results show that only $G_4$ was hydrolyzed to APTS-G 2 as the end product. The APTS-$G_4'$ was resistant to α-amylase-catalyzed hydrolysis due to the presence of the α-(1→6) glucopyranosyl linkage in the non-reducing end of the APTS-$G_4'$.

EXAMPLE 10

The following example is provided to further illustrate the effectiveness of utilizing electrophoresis mediums which are different from prior art borate buffer systems in the analysis of derivatized saccharides. Ten saccharides were derivatized with APTS as generally described in Example 1. Then four different electropherogram were obtained according to the processes of this invention. All of the electropherograms were performed on a 20 µm diameter 27 cm in length untreated fused silica column.

Figure 12:
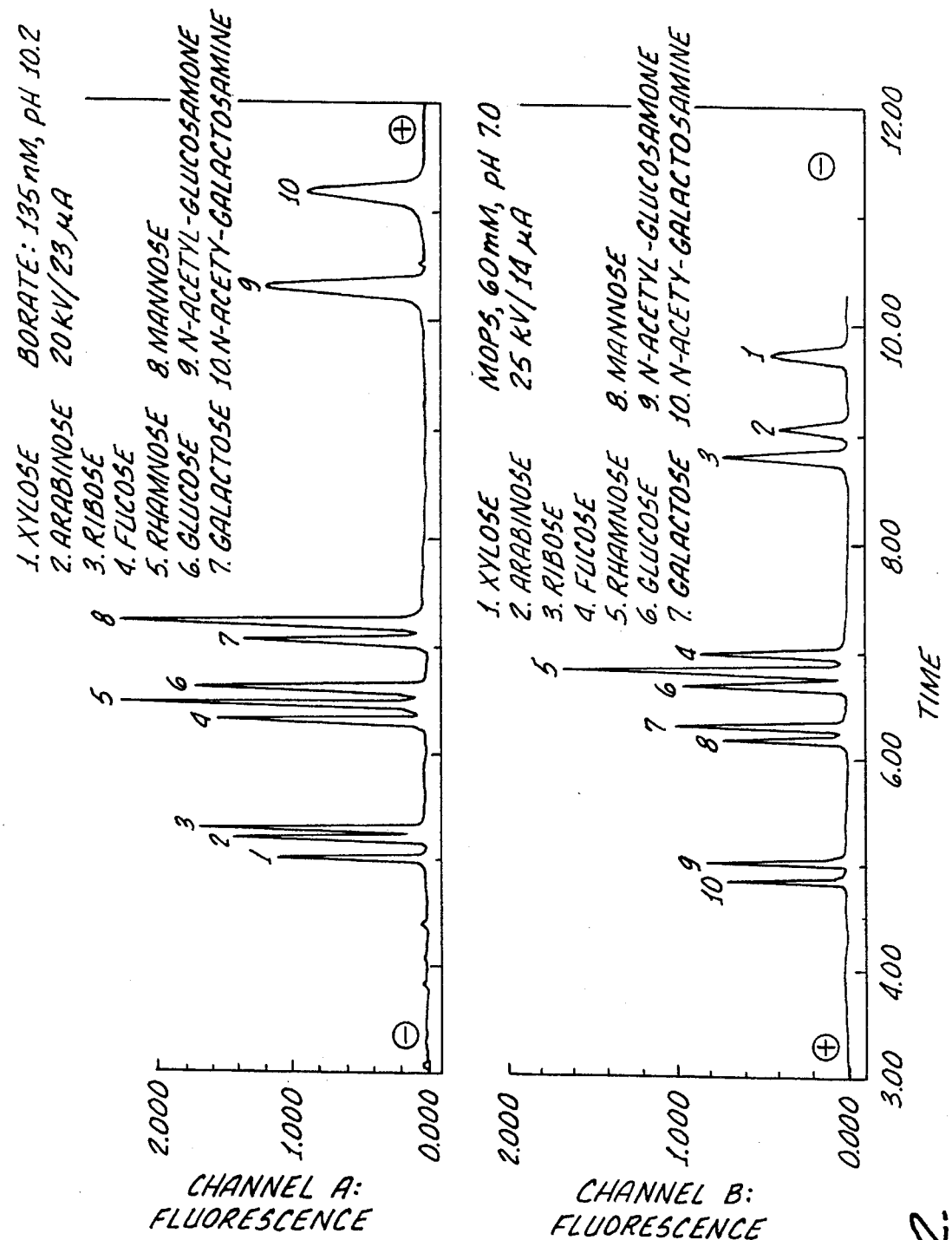
FIG. 12 shows two electropherograms obtained with two different buffer systems. Electropherogram A was performed using a 0.1 M sodium acetate buffer at pH 5.0 using 20 kV/14 μA. Electropherogram B was obtained with 60 mM MOPS (3-morpholinopropanesulfonic acid) at ph 7.0 with 25 kV/14 μA.

FIG. 12 shows two electropherograms obtained with two different buffer systems. Electropherogram A was performed using a 0.1 M sodium acetate buffer at pH 5.0 using 20 kV/14 µA. Electropherogram B was obtained with 60 mM MOPS (3-morpholinopropanesulfonic acid) at pH 7.0 with 25 kV/14 µA. As illustrated the effect of changing buffer was a reverse in the polarity of the column which causes an apparent reversal in the migration order.

Figure 13:
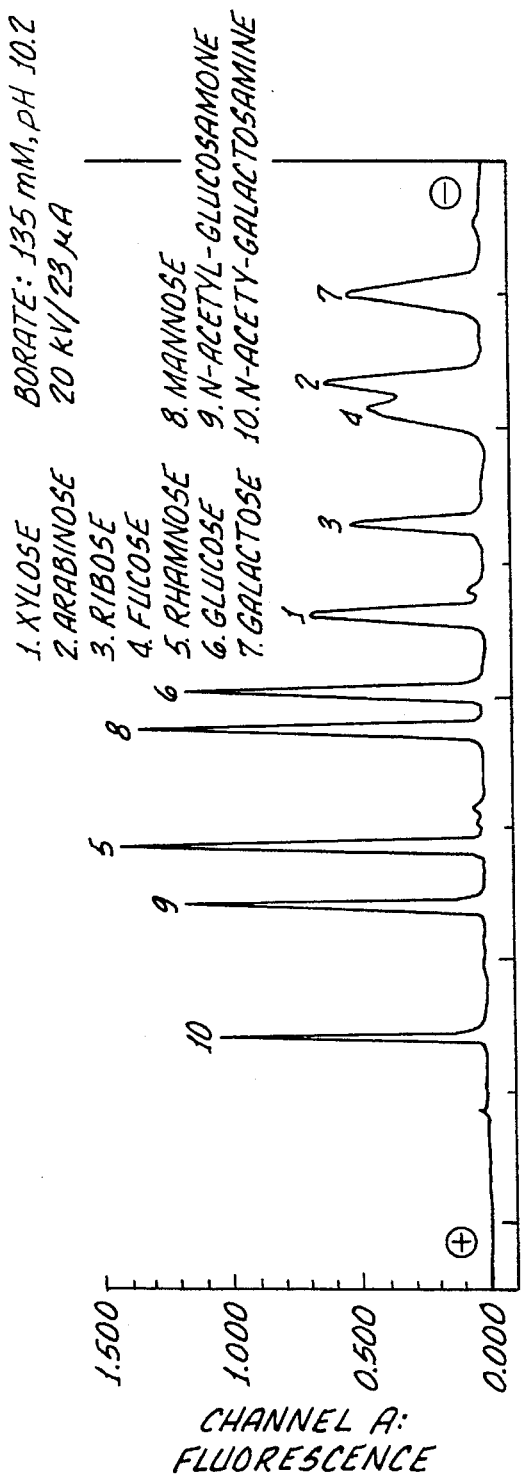
FIG. 13 shows two electropherograms obtained with two different buffer systems. Electropherogram A was performed using a 135 mM borate buffer at pH 10.2 using 20 kV/23 μA. Electropherogram B was obtained with 60 mM MOPS (3-morpholinopropanesulfonic acid) at ph 7.0 with 25 kV/14 μA.
Figure 13:
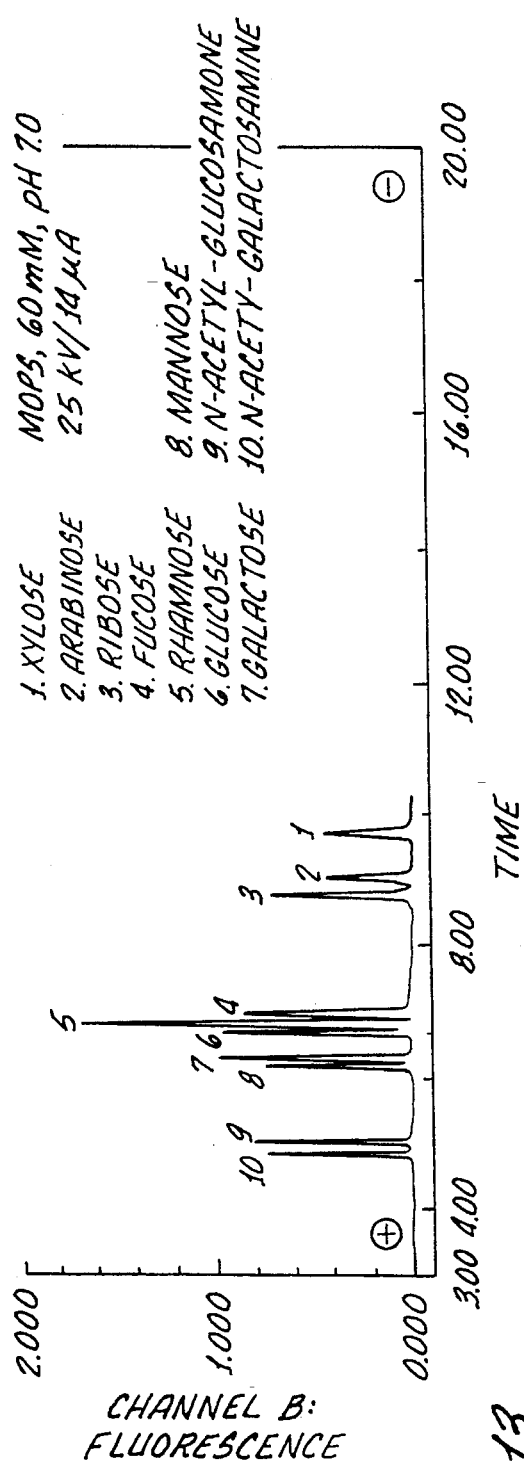

FIG. 13 also shows two electropherograms obtained with two different buffer systems. Electropherogram A was performed using a 135 mM borate buffer at pH 10.2 using 20 kV/23 µA. Electropherogram B was obtained with 60 mM MOPS (3-morpholinopropanesulfonic acid) at pH 7.0 with 25 kV/14 µA. Surprisingly, the traditional borate buffer causes comparatively broad peaks compared with the MOPS buffer. The borate buffer also requires a much longer migration time.

The above examples in combination with the preceding disclosure demonstrate that fluorescent labelled saccharides, oligosaccharides, and polysaccharides can be analyzed with substantially lower detection limits using capillary electrophoresis and laser induced fluorescence. CE-LIF system.

Because of the low detection limits the present invention has tremendous potential in the field of glycobiology and diagnostic applications involving for example diseases related to sugar metabolism.

The foregoing is offered primarily for purposes of illustration. It will be readily apparent to those skilled in the art that modification of the features shown and described herein, as well as variation thereon and substitutions therefor can be made without departing from the spirit and scope of the invention.

We claim:

1. A process for the electrophoretic analysis of monosaccharides and/or polysaccharides, said process comprising the steps of:

providing a composition having derivatized mono and/or polysaccharide components, said derivatized monosaccharide and/or polysaccharide components comprising said monosaccharide and/or polysaccharide labeled with 9-aminopyrene- 1,4,6-trisulfonic acid (APTS) and salts thereof;

introducing said composition into a capillary containing an electrophoretic medium;

applying an electric field across said capillary, said electric field causing said derivatized monosaccharide and/or polysaccharide components to differentially migrate within said electrophoretic medium; and detecting said derivatized monosaccharide and/or polysaccharide components, said detecting accomplished by argon laser exciting said derivatized monosaccharide and/or polysaccharide components and monitoring fluorescent emission of said derivatized monosaccharide and/or polysaccharide components.

2. The process of claim 1 wherein laser exciting said derivatized monosaccharide and/or polysaccharide is accomplished by irradiating said derivatized monosaccharide and/or polysaccharide with coherent radiation of 488 nm.

3. The process of claim 1 wherein monitoring said fluorescent emission is accomplished by detecting radiation emission at 520±20 nm.

4. The process of claim 1 wherein said monosaccharide and/or polysaccharide is selected from the group consisting of reducing sugars, nonreducing sugars, reducing oligosaccharides, nonreducing oligosaccharides, reducing polysaccharides, and nonreducing polysaccharides.

5. A process for the electrophoretic analysis of monosaccharides and/or polysaccharides, said process comprising the steps of:

providing a composition having derivatized mono and/or polysaccharide components, said derivatized monosaccharide and/or polysaccharide components comprising said monosaccharide and/or polysaccharide labeled with a fluorescing charged compound selected from the group consisting of APTS;

introducing said composition into a capillary column, said capillary column containing an electrophoresis medium;

applying an electric field across said capillary column, said electric field capable of causing said derivatized monosaccharide and/or polysaccharide components to differentially migrate within said electrophoretic medium; and detecting said derivatized monosaccharide and/or polysaccharide components, said detecting accomplished by laser exciting said derivatized monosaccharide and/or polysaccharide components with an argon ion laser at 488 nm and monitoring fluorescent emission of said derivatized monosaccharide and/or polysaccharide components at 520±9 nm.

6. The process of claim 5 wherein said electrophoretic medium is a buffer solution selected from the group consisting of borate buffer solutions, phosphate buffer solutions, morpholine buffer solutions, and acetate buffers solutions.

7. A process for the electrophoretic analysis of monosaccharides and/or polysaccharides, said process comprising the steps of:

providing a composition having derivatized mono and/or polysaccharide components, said derivatized monosaccharide and/or polysaccharide components comprising said monosaccharide and/or polysaccharide labeled with a fluorescing charged compound;

introducing said composition into an electrophoretic medium contained within a capillary column, said electrophoretic medium selected from the group consisting of and morpholine buffer solutions;

applying an electric field across said electrophoretic medium, said electric field capable of causing said derivatized monosaccharide and/or polysaccharide components to differentially migrate within said electrophoretic medium; and detecting said derivatized monosaccharide and/or polysaccharide components, said detecting accomplished by exciting said derivatized monosaccharide and/or polysaccharide components with argon laser radiation and monitoring fluorescent emission of said derivatized monosaccharide and/or polysaccharide components.

8. The process of claim 7 wherein said fluorescing compound is selected from the group consisting of APTS and 8-aminonaphthalene- 1,3,6-trisulfonic acid (ANTS).

* * * * *